US005084482A

United States Patent [19]

Hirsch et al.

[11] Patent Number: 5,084,482

[45] Date of Patent: Jan. 28, 1992

[54] METHODS FOR INHIBITING INFLAMMATORY ISCHEMIC, THROMBOTIC AND CHOLESTEROLEMIC DISEASE RESPONSE WITH METHIONINE COMPOUNDS

[75] Inventors: Gerald P. Hirsch, Atlanta, Ga.; Robert K. Bayless, Austin, Tex.

[73] Assignee: The Lithox Corporation, Austin, Tex.

[21] Appl. No.: 508,104

[22] Filed: Apr. 10, 1990

[51] Int. Cl.[5] .................... A61K 31/195; A61K 31/20

[52] U.S. Cl. .................................... 514/562; 514/59; 514/249; 514/260; 514/346; 514/458; 514/474; 514/494; 514/501; 514/532; 514/550; 514/559; 514/725; 514/727; 424/641; 424/702

[58] Field of Search ............... 514/562, 501, 346, 249, 514/559, 260, 532, 59, 725, 474, 458, 494, 727, 562, 550; 424/641, 702

[56] References Cited

U.S. PATENT DOCUMENTS

| | | | |
|---|---|---|---|
| 3,952,115 | 4/1976 | Damico et al. | 426/615 |
| 4,315,028 | 2/1982 | Scheinberg | 424/290 |
| 4,711,780 | 12/1987 | Fahim | 514/562 |
| 4,927,850 | 5/1990 | Bayless et al. | 514/458 |

FOREIGN PATENT DOCUMENTS 2821704 11/1978 Fed. Rep. of Germany .

OTHER PUBLICATIONS

Gualano, Pharmacol Research Comm 15:683-96 (1983).

Flynn et al., Inflammation 8:33-44 (1984).

Poston et al., Atherosclerosis 19:353-67 (1974).

Ambanelli, U., Sposni, A., Ferraccioli, G., Serum Antioxidant Activity and Related Variables in Rheumatoid Arthritis, Scand. J. Rheumatology, 11: 203-7, 1982.

Ames, B., Dietary Carcinogens and Anticarcinogens, Science, 221: 1256-64, 1983.

Bailey, K., Sheffner, A., The Reduction of Experimentally Induced Inflammation by Sulfhydryl Compounds, Biochemical Pharmacology, 16: 1175-82, 1967.

Baldessarini, R., Stramentionoli, G., Lipinski, J., Methylation Hypothesis, Archives of General Psychiatry, 36: 303-7, 1979.

Brattstrom, L., Israelsson, B., Jeppsson, J. Hultberg, B., Folic acid—an innocuous means to reduce plasma homocysteine, Scand. J. Clin. Lab. Invest., 48: 215-21, 1988.

Braughler, J., Hall, E., Central Nervous System Trauma and Stroke I Free Radical Biology & Medicine, 6: 289-301, 1989.

Carp, H., Mitochondrial N-Formylmethionyl Proteins as Chemoattractants for Neutrophilis, J. Exp. Medicine, 155:264-75, 1982.

Cho., E., Andersen, B., Filer, L., Stegink, L. D-Methionine Utilization in Young Miniature Pigs, Adult Rabbits, and Adult Dogs, J. Parenteral and Enteral Nutrition, 4: 544-7, 1980.

Connor, H., Newton, D., Preston, R., Woods, H., Oral Methionine Loading as a Cause of Acute Serum Folate Deficiency: Its Relevance to Parenteral Nutrition, Postgraguate Medical J., 54: 318-20, 1978.

Cross., C., Halliwell, B., Borish, E., Pryor, W., Ames, B., Saul, R., McCord, J., Harman, D., Oxygen Radicals and Human Disease, Annals of Internal Medicine, 107: 526-45, 1987.

Cuperus, R., Muijsers, A., Wever, R., Antiarthritic Drugs Containing Thiol Groups Scavenge Hypochlorite and Inhibit its Formation by Myeloperoxidase from Human Leukocytes, Arthritis and Rheumatism, 28: 1228-33, 1985.

Cybulsky, M., Chan., M., Movat, H., Acute Inflammation and Microthrombosis Induced by Endotoxin, Interleukin-1, and Tumor Necrosis Factor and their Implication in Gram-Negative Infection. Laboratory Investigation, 58: 365-78, 1988.

Davis., R., Inhibition of Inflammation with Certain Amino Acids, J. of the Am. Podiatry Assoc., 68: 24-30, 1978.

Delrieu, F., Ferrand, B., Amor, B., Etude Preliminaire de La L-Methionine dans le Traitement de La Polyarthrite Rhumatoide, Revue du Rhumatisme, 55: 995-7, 1988.

Eisenhauer, L., Gerald, M., The Nurse's 1984-85 Guide to Drug Therapy, Prentice-Hall, New Jersey, 1984, pp. 247-65, and 584-602.

Figge, H., Figge, J., Souney, P., Mutnick, A., Sachs, F., Nicotinic Acid: A Review of its Clinical Use in the Treatment of Lipid Disorders, Pharmacotherapy, 8: 287-94, 1988.

Fleisher, L., Gaull, G., Methionine Metabolism in Man: Development and Deficiencies, Clinics in Endocrinology and Metabolism, 3:37-55, 1974.

Flynn, P., Becker, W., Vercellotti, G., Weisdorf, D., Craddock, P., Hammerschmidt, D., Lillehei, R., Jacob, H., Ibuprofen Inhibits Granulocyte Responses to Inflammatory Mediators. Inflammation 8: 33-44, 1984.

(List continued on next page.)

*Primary Examiner*—Frederick E. Waddell
*Assistant Examiner*—Diane Gardner

[57] ABSTRACT

This invention concerns novel methods employing compositions containing as an active antioxidant or antiinflammatory agent the amino acid methionine, and/or one or more related compounds including certain metabolic precursor compounds, for treating or inhibiting inflammatory ischemic, thrombotic and cholesterolemic disease response in a subject. The compounds include the methionine hydroxy analogs, as well as compounds having the structural formula I:

$$CH_3S(CH_2)_n-\underset{\displaystyle NH_2}{\underset{|}{CH}}-COOH$$

l-, dl- or d- form and pharmaceutically acceptable N-(mono- and di-carboxylic acid) acyl derivatives and alkyl esters thereof, where n is an integer from 1 to 3.

16 Claims, No Drawings

OTHER PUBLICATIONS

Gualano, M., Stramentinoli, G., Berti, F., Anti-Inflammatory Activity of S-Adenosyl-L-Methionine: Interference with the Eicosanoid System Pharmacological Research Communications, 15: 683-96, 1983.

Hall, E., Braughler, J., Central Nervous System Trauma and Stroke II. Free Radical Biology & Medicine, 6: 303-13, 1989.

Hall, N., Blake, D., Bacon, P., Serum Sulphydryl Levels in Early Snyovitis, J. of Rheumatology, 9: 593-6, 1982.

Inoue, Y., Zama, Y., Suzuki, M., D-Amino Acids as Immunosuppressive Agents, Japanese J. Exp. Medicine, 51: 363-6, 1981.

Johnson, J., Sustained Release Medications, Noyes Data Corp., New Jersey, 1980, p. 14.

Kies, C., Fox, H., Aprahamian, S., Comparative Value of L-, DL—, and D-Methionine Supplementation of an Oat-based Diet for Humans, J. of Nutrition, 105: 809-14, 1975.

Malinow, M., Kang., S., Taylor, L., Wong., P., Coull, B., Inahara, T., Mukerjee, D., Sexton, G., Upson, B., Prevalence of Hyperhomocyst(e)inemia in Patients with Peripheral Arterial Occlusive Disease, Circulation, 79: 1180-8, 1989.

Marcolongo, R., Giordano, N., Colombo, B., Cherie--Ligniere, G., Todesco, S., Mazzi, A., Mattara, L., Leardini, G., Passeri, M., Cucinotta, D., Double-Blind Multicentre Study of the Activity of S-Adenosyl-Methionine in Hip and Knee Osteoarthritis, Current Therapeutic Research, 37: 82-94, 1985.

McKenna, F., Hickling P., Kixon, J., Bird, H., Methylcycsteine in Rheumatoid Arthritis, Br. J. of Rheumatology, 25: 132, 1986.

Middeke, M., Holzgreve, H., Review of Major Intervention Studies in Hypertension and Hyperlipidemia: Focus on Coronary Heart Disease, Am. Heart J., 116: 1708-12, 1988.

Montgomery, R., Dryer, R., Conway, T., Spector, A., Biochemistry: A Case-Oriented Approach Mosby Co., St. Louis, 4th Ed., 1983, pp. 466-70.

Munro, J., Cotran, R., The Pathogenesis of Atherosclerosis: Atherogenesis and Inflammation, Laboratory Investigation, 58: 249-61, 1988.

O'Brien, J., Destruction of Elastic Tissue (Elastolysis) as a Link between Atherosclerosis and the Temporal Arteritis/Polymyalgia Rheumatica Syndrome, Pathologie Biologie, 32: 123-38, 1984.

Olszewski, A., Szostak, W., Homocysteine Content of Plasma Proteins in Ischemic Heart Disease, Atherosclerosis, 69: 109-13, 1988.

Plow, E., Edgington, T., I. The Cleavage of Fibrinogen by Leukocyte Proteases at Physiologic pH, J. of Clinical Investigation, 56: 30-8, 1975.

Poston, R., Davies, D., Immunity and Inflammation in the Pathogenesis of Atherosclerosis, Atherosclerosis, 19: 353-67, 1974.

Reinhold, J., Lahimgarzadeh, A., Nasr, K., Hedayati, H., Effects of Purified Phytate and Phytate-Rich Bread upon Metabolism of Zinc, Calcium, Phosphorus, and Nitrogen in Man, The Lancet, Feb. 10, 1973, pp. 283-8.

Remington's Pharmaceutical Sciences, Gennaro, A., Editor. Phil. College of Pharm. and Sci., 17th Edition, 1985, pp. 773-85, 819-23, 1542-50, 1585-602.

Ross, R., The Pathogenesis of Atherosclerosis—an Update, New Eng. J. of Medicine, 314: 488-500, 1986.

Rotruck, J., Boggs, R., Comparative Metabolism of L-Methionine and N-Acetylated Derivatives of Methionine, J. Nutrition, 105: 331-7, 1975.

Rubin, R., Ordonez, L., Wurtman, R., Physiological Dependence of Brain Methionine and S-Adenosyl--Methionine Concentration on Serum Amino Acid Pattern, J. of Neurochemistry, 23: 227-31, 1974.

Sarwar, G., Peace, R., Comparisons between True Digestibility of Total Nitrogen and Limiting Amino Acids in Vegetable Proteins Fed to Rats, J. of Nutrition, 116: 1172-84, 1986.

Schlievert, P., Shands, K., Dan, B., Schmid, G., Nishimura, D., Identification and Characterization of an Exotoxin from Staphylococcus aureus Associated with Toxic-Shock Syndrome, J. of Infectious Diseases, 143: 509-16, 1981.

Spector, W., An Introduction of General Pathology, 2nd Edition, Churchill Livingstone, New York, 1980, pp. 58-75.

Stegink, L., Bell, E., Filer, L., Siegler, E., Andersen, D., Seligson, F., Effects of Equimolar Doses of L-Methionine, D-Methionine and L-Methionine-dl-Sulfoxide on Plasma and Urinary Amino acid Levels in Normal Adult Humans, J. Nutrition, 116: 1185-92, 1986.

Stegink, L., Filer, L., Baker G., Plasma Methionine Levels in Normal Adult Subjects after Oral Loading with L-Methionine and N-Acetyl-L-Methionine, J. Nutrition, 110: 42-9, 1980.

Stendahl, O., Coble, B., Dahlgren, C., Hed, J., Molin, L., Myeloperoxidase Modulates the Phagocytic Activity of Polymorphonuclear Neutrophil Leukocytes. Studies with Cells from a Myeloperoxidase-deficient Patient, J. Clinical Investigation, 73: 366-73, 1984.

Stramentinoli, G., Pharmacologic Aspects of S-Adenosylmethionine, Am. J. of Medicine, 83(Suppl 5A): 35-42, 1987.

Sugiyama, K., Kushima, Y., Muramatsu, K., Effects of Sulfur-containing Amino Acids and Glycine on Plasma Cholesterol Level in Rats Fed on a High Cholesterol Diet, Agric. Biol. Chem., 49: 3455-61, 1985.

Truswell, A., McVeigh, S., Mitchell, W., Bronte-Stewart, B., Effect in Man of Feeding Taurine on Bile Acid Conjugation and Serum Cholesterol Levels, J. of Atherosclerosis Research, 5: 526-32, 1965.

Tsan, M., Chen, J., Oxidation of Methionine by Human Polymorphonuclear Leukocytes, J. Clinical Invest., 65: 1041-50, 1980.

Vedder, N., Winn, R., Rice, C., Harlan, J., Neutrophil-Mediated Vascular Injury in Shock and Multiple Organ Failure, Perspectives in Shock Research: Metabolism, Immunology, Mediators, and Models, Liss, Inc., 1989, pp. 181-191.

Weissmann, G., Smolen, J., Hoffstein, S., Polymorphonuclear Leukocytes as Secretory Organs of Inflammation, J. of Investigative Dermatology, 71: 95-9, 1978.

Weitzman, S., Weitberg, A., Phagocytes as Carcinogens: Malignant Transformation Produced by Human Neutrophils, Science, 227: 1231-3, 1985.

Yamada, O., Moldow, C., Sacks, T., Craddock, P., Boogaerts, M., Jacob, H., Deleterious Effects of Endotoxin on Cultured Endothelial Cells: An in Vitro Model of Vascular Injury, Inflammation, 5: 115-26, 1981.

Yamori, Y., Wang, H., Ikeda, K., Kihara, M., Nara, Y., Horie, R., Role of Sulfur Amino Acids in the Prevention and Regression of Cardiovascular Diseases, Sulfur Amino Acids: Biochemical and Clinical Aspects, Liss, Inc., New York, 1983, pp. 103-15.

METHODS FOR INHIBITING INFLAMMATORY ISCHEMIC, THROMBOTIC AND CHOLESTEROLEMIC DISEASE RESPONSE WITH METHIONINE COMPOUNDS

This application is a continuation-in-part of Application Ser. No. 07/179,226, filed on Apr. 8, 1988 now abandoned.

TECHNICAL FIELD

This invention concerns novel methods employing antioxidant and antiinflammatory dietary or therapeutic compositions containing the amino acid methionine (also known as "Met"), and/or one or more related compounds including certain metabolic precursor compounds for inhibiting inflammatory ischemic, thromboticand cholesterolemic disease response in man and animals.

BACKGROUND OF THE INVENTION

A variety of efforts have been made over many years to elucidate the mechanisms and origins of inflammation and the various forms of disease it may cause. Limited success has been achieved in alleviating the symptoms of diseases having inflammatory components. Oxidative stress has been implicated in many of these diseases, and antioxidant therapy has been recommended as one method to alleviate the damage it causes (Cross, et. al., Annals of Internal Medicine, 107:526–45, 1987).

Recently, several investigators have focused on the role of sulfhydryl compounds in the mechanism of treatment of some forms of arthritis. Cuperus, (Arthritis and Rheumatism 28: 1228–33 1985) showed that d-penicillamine, tiopronin, aurothiomalate and aurothioglucose were scavengers of the products of activated granulocytes, and Bailey and Sheffner (Biochemical Pharmacology 16: 1175–82, 1967) showed that acetylcysteine and acetylpenicillamine reduced experimental dermal inflammation but that methionine did not. Methionine is known to be oxidized to its sulfoxide by granulocytes but not by hydrogen peroxide at physiological concentrations. Persons deficient in the enzyme myeloperoxidase do not make hypocholorous acid in lymphocytes and appear not to suffer unusually from infections. By contrast, persons with deficient production of hydrogen peroxide are adversely affected. (Stendahl, et al., J. Clin. Invest., 73:366–73, 1984).

Cuperus, supra, describes a feature of inflammed synovial fluid, such as that occurring in arthritis patients, as the accumulation of polymorphonuclear (PMN) leukocytes. One function of the leukocytes is the destruction of invading elements such as microorganisms. For this destruction, the leukocyte releases hydrogen peroxide and enzymes, e.g., myeloperoxidase, into the extracellular fluid. In the presence of hydrogen peroxide and chloride ion, myeloperoxidase catalyzes the formation of reactive hypochlorous acid (HOCl) which can oxidize tissue components and plasma protease inhibitors. Oxidation and subsequent inactivation of these protease inhibitors in vivo may lead to unrestrained proteolysis, resulting in severe tissue damage. (Weissmann, et.al., Jour. Investigative Dermatology, 71:95–9, 1978).

Several investigators have noted that patients with severe rheumatoid arthritis have lower levels of serum SH groups (Hall, Journal of Rheumatology 9:593–6, 1982). Ambanelli (Scand. Jour. Rheumatology 11:203–7, 1982) showed that serum SH groups went up in patients that responded to tiopronin therapy. The mechanism of serum SH groups in relation to the severity of arthritis has not been established. The correlation could be explained by the failure of particular individuals to counteract the production of oxidizing substances by immunocytes.

McKenna, (British J. Rheumatology 25:132, 1986), saw benefit for only 2 of 15 patients given cysteine methyl ester for rheumatoid arthritis, a direct sulfhydryl agent.

Delrieu, et al., (Revue du Rhumatisme, 55:995–7, Dec., 1988) found no statisical difference between treatment and controls in a 24 patient study of rheumatoid arthritis using 5 and 10 grams of l-methionine per day for 4 and 2 months, respectively. Clinical tolerance was good, but gastrointestinal distress was encountered by a majority of the patients.

Gualano (Pharmacology Research Comm. 15:683–96, 1983) showed antiinflammatory activity of S-adenosyl methionine but attributed its effects to mechanisms of aspirin-like drugs. Davis, (Jour. Am. Pod. Assoc. 68:24–30, 1978) studied the effects of certain amino acids on inflammation measured as edema and found that methionine was not effective in reducing edema while cystine was effective. Marcolongo (Current Therapeutic Research 37:82–94, 1985) showed beneficial effects of S-adenosyl methionine slightly better than ibuprofen in the treatment of hip and knee osteoarthritis. Stramentinoli (Am. Jour. Medicine, 83 Suppl 5A:35–42, 1987) shows that S-adenosyl methionine will inhibit the swelling in carrageenin-induced rat paw edema, while l-methionine in equimolar doses is completely ineffective.

Other studies involving the oral administration of S-adenosyl methionine have shown that treatment does not increase the blood levels of methionine (Baldessarini, et. al., Arch. Gen. Psychiatry, 36:303–7, 1979). In animal studies blood level increases of methionine are reflected by parallel increases in brain levels of methionine, but a 10 fold increase in brain methionine produces only a 50% increase in brain S-adenosyl methionine (Rubin, et al., J. Neurochemistry 23: 227–231, 1974).

In a study of the immunosuppressive activity of D-amino acids, Inoue, et al. showed that there was no immunosuppressive effect for d-methionine in their mouse assay at a dose of 10 mg per kg body weight. (Japanese J. Experimental Medicine, 51:363–6, 1981).

Regarding acute inflammation, the complement system of the human body (see Spector, W. G., Intro. to General Pathology, p. 58–75, Churchill Livingstone, New York, 1980) is part of a cascade of enzyme reactions that are responsive to external injury in which complement is activated and generates peptides known as C3a and C5a which are response-inducing or chemotactic for white cells.

The S-methyl derivative of methionine, S-methyl methionine, also known as vitamin U has been shown to have benefit as an anti-ulcer compound and to have benefit for allergies. The same benefit is shown for carboxyl esters and N-acyl derivatives (Kowa, DT 2821-704). However, in this teaching no distinction is made for the d- and l-isomers of S-methyl methionine or its derivatives and no claim is made that these compounds act through anti-inflammatory mechanisms.

INFLAMMATORY ISCHEMIA AND THROMBOSIS

O'Brien (Pathologie Biologie, 32:123–38, 1984) and Munro and Cotran (Laboratory Investigation, 58:249–61, 1988) reviewed the evidence for the contribution of elastolysis to atherosclerosis including a contribution for leukocyte infiltration in eventual plaque development. A more significant contribution of immune cells in atherosclerosis was shown by Poston and Davies (Atherosclerosis, 19:353–67, 1974) wherein they point out the following evidence for etiology of ischemic vascular disease:

1. The development of rabbit atherosclerosis can be inhibited by antiinflammatory and immunosuppressive drugs.
2. Arthritis can be produced experimentally by immune complexes.
3. Milk antibodies are increased in persons with myocardial infarction.
4. Autoantibodies to arterial tissue have been found in ischemic vascular disease.
5. Half of young adults dead from coronary accidents have acute inflammatory changes.
6. Eighty-two percent of young adults with atherosclerotic lesions have inflammatory changes in small branches of coronary arteries.
7. Rabbits (50%) develop aortic lesions after being given a bovine serum injection when on a 1% cholesterol diet.
8. Atherosclerosis develops in coronary arteries of transplanted hearts 19 months before death of the recipient.

Leukocytes accumulate in complex thrombi that consist of fibrin and platelets (Plow and Edginton, Jour. of Clinical Investigation, 56:30–8, 1975; and Cybulsky, Chan, Movat; Laboratory Investigation 58:365–78, 1988).

Ibuprofen, an antiinflammatory drug, inhibits the response of granulocytes to inflammatory mediators and has been shown to reduce the size of infarct after experimental ligation of the anterior descending artery. Thus, inflammation is implicated in the ischemia and resultant cell destruction that occur after blood flow has ceased (Flynn et al.; Inflammation, 8:33–44, 1984). Cardiac muscle mitochondrial N-Formylmethionyl proteins, released after myocardial injury, are chemoattractants for PMN's (Carp; Jour. Experimental Medicine, 155:264–75, 1982). Ischemia following reperfusion in cardiac arrest or CNS injury results from generation of oxygen radicals. PMNs activated by cellular injury can expose injured tissues to high local concentrations of oxidants. For a review, see Braughler and Hall (Free Radical Biology and Medicine, 6:289–301, 1989) and Hall and Braughler (Free Radical Biology and Medicine, 6:303–13, 1989).

INFLAMMATORY SYMPTOMS OF SHOCK

Toxic-shock syndrome (TSS) is caused by a bacterial toxin, and occurs mainly in young menstruating women (Schlievert, et al., J. Infectious Diseases, 143:509–16, 1981). The PMN may be the common pathway through which inflammatory mediators act in septic shock, causing multiple organ failure. Aseptic shock, which is mainly reperfusion injury as blood flow returns to the area, also depends on the PMN for mediation (Vedder, et.al., Perspectives in Shock Research: Metabolism, Immunology, Mediators, and Models, Alan R. Liss, p. 181–91, 1989). Endotoxin has been shown to stimulated PMNs to release large amounts of toxic oxygen species which cause tissue and organ damage (Yamada, et. al., Inflammation, 5:115–26, 1981).

LIPID METABOLISM NORMALIZATION

Heart attacks and strokes are the major killers of man in the industrial world (Ross, New Eng. Jour. Med., 314:488–500, 1986). Efforts to reduce the incidence have concentrated on altering the diet by reduction of salt and fat consumption, especially saturated fat and cholesterol, and by increase of exercise with corresponding weight control. Increased consumption of bran has been touted as a method to reduce serum cholesterol levels, but the phytate in bran can cause zinc deficiency and reduced calcium absorption from the diet. (Reinhold, et al., The Lancet, Feb. 10, 1973, p. 283–8). High serum concentrations of low-density lipoprotein cholesterol is considered a major risk factor for coronary heart disease (CHD). Lowering hypertension without concomitant decrease of serum cholesterol has little influence on CHD. (Middeke, and Holzgreve, Am. Heart J., 116:1708–12, 1988). Nicotinic acid (vitamin B3) is the first-line drug for the treatment of patients with primary hypercholesterolaemia. Side-effects of the typical daily dose of 3 to 5 grams a day are flushing, nausea, cramps and diarrhoea (Figge, et al., Pharmacotherapy 8:287–94, 1988).

Truswell et al., (J. Atheroscler. Research, % :526–32, 1965) show that in humans administration of 1.5 grams of taurine per day for 15 days produced no effect on serum cholesterol concentrations.

DIETARY DEFICIENCY OF METHIONINE

Methionine deficiency is not recognized as a disease state in modern countries where adequate total protein is generally available. While it is recognized that humans, in contrast to most other mammals, cannot utilized d-methionine as a source of methionine, it is generally assumed that humans can utilized methionine sulfoxide as a source of methionine. The only suggestion that methionine sulfoxide might not be nutritionally equivalent to methionine is the lack of increase of blood l-methionine after administration of l-methionine sulfoxide. Human enzymes have been found that can reduce methionine sulfoxide to methionine.

Methionine is known to be affected by a variety of food processing activities. l-Methionine is converted to d-Methionine when proteins are heated and a significant amount of the nutritional value of methionine can be lost by this mechanism. However, most of the potential loss of available methionine occurs through the mechanism of oxidation of methionine to methionine sulfoxide. The bleaching of flour is the major cause, when during the process of bleaching the chlorine is able to react with methionine. When proteins are heated with reducing sugars methionine is readily oxidized so that items such as canned peaches are potential sources of food with a deficiency of available methionine. More recently, as unsaturated fats replace saturated fats in prepared food sources additional sources of methionine oxidation occur. For example, the unsaturated fats in cake mixes held in a hot warehouse would result in oxidation of methionine to its sulfoxide. Published evidence for an extensive loss of methionine in food processing as regards human nutrition occured in the manufacture of instant oatmeal where the product used in nitrogen balance studies apparently had no nutritionally available methionine (see Kies, et. al., J. Nutrition, 105: 809–14, 1975). In the cooking of several types of beans 40% to 50% of the methionine is not available to rats (Sawar and Peace, J. Nutrition, 116:1172–84, 1986). The dietary requirement for methionine plus cysteine is based on nitrogen balance studies where a total of 800 mg per day is required to bring 50% of adults into positive nitrogen balance. No attempt has been made to determine the level of methionine that might be optimal for the prevention of oxidative damage.

Discussion

Methionine has been shown to be a target for the products of stimulated polymorphonuclear neutrophils (Tsan and Chen, J. Clin. Invest., 65:1041–50, 1980). The granular fraction of the PMNs oxidizes methionine to its sulfoxide in the presence of peroxide. Peroxide does not oxidize methionine to its sulfoxide at normal physiological concentrations.

Some of the differences measured in the relative effectiveness of methionine compounds and other chemicals especially in sulfhydryl reducing substances may be attributed to the control mechanisms that operate in animals and man to regulate the amounts of these substances wherein giving more of a substance does not significantly increase blood and tissue levels of that substance. Stegink, (Jour. Nutrition,116:1185–92, 1986), showed that 0.5 gm of methionine elevated total blood methionine 2-fold for 2 hours with l-methionine but 3-fold for 4 hours with d-methionine. In the same study it was shown that methionine sulfoxide administration did not result in elevation of blood methionine. This observation suggests that methionine sulfoxide is not readily reduced to methionine but it is possible that this reduction occurs in tissues where the methionine remains sequestered. l-Methionine is an essential amino acid for human nutrition. The normal serum level of methionine in man is 15 ppm. dl-Methionine is available as a one-a-day food supplement in 500 mg. oral tablet form.

Regarding human nutrition, l-methionine is an essential amino acid whereas d-methionine is non-nutritive. For purposes of metabolism, l-methionine via S-adenosylmethionine has an important methylating function. In this function it loses a methyl group from its sulfur atom to become homocysteine. Homocysteine, as is known, when in excess can lead to homocysteinuria, and may be heart disease associated (Malinow, et al., Circulation 79:1180–88, 1989) and (Olszewski and Szostak, Atherosclerosis 69:109–13, 1988). Folic acid has been shown to be an innocuous method to reduce plasma homocysteine levels (Brattstrom et al., Scand. J. Clin. Lab. Invest. 48:215–221, 1988). Administration of 8 grams of l-methionine to adult subjects for four days caused a greater than 30% reduction in serum folate levels (Conner, et al., PostGrad. Med. J. 54:318–20, 1978). Thus, folate should be co-administered whenever methionine is chronically consumed.

Administration of large amounts (5 to 10 grams per day) of l-methionine can cause gastrointestinal upset. Many people report a burning sensation in the stomach after taking methionine, along with an upset stomach and flatulance (Delrieu, et al, Revue du Rhumatisme, 55: 995–7, 1988). Enteric coating and timedrelease formulations should avoid the stomach problems and allow even elevations of blood methionine for maximum antioxidant effect. Typical enteric coating agents include cellulose acetate phthalate, and other cellulose ethers and derivatives (Johnson, J. C., in Sustained Release Medications, Noyes Data Corp, New Jersey, 1980, p.14).

The Food and Nutrition Board of the U.S. National Academy of Sciences has established the Recommended Daily Allowance (RDA) for nutrients for most healthy individuals. For a discussion, see The Nurses Guide to Drug Therapy, Eisenhauer and Gerald, Prentice-Hall, New Jersey, 1984–5, pages 584–602, and incorporated here by reference. RDA's include: Vitamin A: 5000 I.U.; Vitamin B12: 3 mcg.; Vitamin B6: 2 mg; Vitamin B3: 18 mg.; Folic Acid: 400 mcg.; Vitamin C: 100 mg.; Vitamin D: 400 I.U.; Vitamin E: 15 I.U.; Calcium: 800–1200 mg.; Iron: 18 mg.; Selenium: No RDA has been established, but the maximum non-toxic suggested dose is 200 mcg. per day; Zinc: 15 mg. For a review of life-style risk factors and protective factors in the diet, see the article by Bruce N. Ames entitled "Dietary Carcinogens and Anticarcinogens", Science, 221:1256–63, 1983, incorporated here by reference.

Different species utilize d-forms of amino acids to different extents. Humans and monkeys utilize d-methionine poorly while pigs, dogs, rabbits, chickens, rats and mice use d-methionine as a sulfur source fairly well. Animals do not metabolize N-blocked-d-methionine as they do N-blocked-l-methionine. Some N-blocking groups are not cleaved by enzymes that remove common blocking groups such as acetyl groups (Cho, Jour. Parenteral and Enteral Nutrition 4: 544–7, 1980; Stegink, Jour. of Nutrition 110: 42–9, 1980; Rotruck, Jour. of Nutrition 105: 331–7, 1975).

The patent to Scheinberg U.S. Pat. No. 4,315,028 describes a method of treatment of arthritis employing substituted cysteines.

The patent to Kowa (DT 2821-704) describes antiulcer activity and antiallergy benefits for the S-methyl derivative of methionine and methionine esters and N-acyl derivatives. The d- and l- isomers of S-methyl methionine compounds and derivatives are not distinguished.

The patent to Damico U.S. Pat. No. 3,952,115 describes foodstuffs containing N-acyl l-methionine esters and N-acyl l-cysteine esters. d-Isomers are specifically excluded because they are "not nutritionally available".

The patent to Fahim, U.S. Pat. No. 4,711,780, shows the benefit of the combination of cysteine with vitamin C and zinc salts in a topical mixture for stimulating cell proliferation. The benefit of methionine is claimed but not shown. No demonstration of benefit or claim for systemic administration is made.

In view of the widespread incidence of diet-related vascular disease and inflammation, a need exists for means, other than diet alone, of preventing or inhibiting the incidence and serious consequences of the disease. Thus there is a need at present for means of treating disease conditions of the kind in which a nutritional deficiency, an inflammatory response or abnormal inflammation is implicated.

It is therefore an object of the present invention to provide methods for the prevention, inhibition and treatment of disease conditions of man and animals that may be attributable to or result from nutritional deficiency and inflammatory responses.

It is a further object of the invention to provide means for preventing or alleviating symptoms of homocysteinuria that may result from excess methionine intake.

These and other objects, features and advantages will be seen from the following detailed description of the invention.

SUMMARY AND DETAILED DESCRIPTION OF THE INVENTION

Our invention is based on the discovery that certain methionine or methionine-type compounds in the dl-form or d-form at relatively high, well-tolerated doses are potent antioxidant and antiinflammatory agents in man and animals. The invention includes means for inhibiting or treating conditions predisposing to or presenting as an inflammatory ischemic or thrombotic disease response in man and animals. The methionine compounds in high daily dosage according to the invention thus may act in vivo to inhibit oxidative effects such as the action of hypochlorous acid to reduce proteolysis and tissue damage.

Novel methods for the prevention and treatment of disease conditions of man and animals that may be attributable to or result from nutritional deficiency of the l-form of methionine, such as lipid abnormalities, are also disclosed.

The inclusion of the amino acids glycine and serine and the vitamins B6, B12 and folate for homocysteine normalization are also disclosed.

For purposes of the invention, one uses at least one methionine-type compound selected from the methionine hydroxy analogs and methionine compounds having the structural formula I

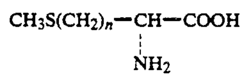

I l-, dl or d form and pharmaceutically acceptable N- (mono- and dicarboxylic acid) acyl derivatives and alkyl esters thereof, where n is an integer from 1 to 3.

Thus, the methionine-type compound (for convenience sometimes referred to herein as "methionine" or "methionine compound") may be normethionine ($n=1$), methionine ($n=2$), homomethionine ($n=3$), the hydroxy analog, or the acyl or alkyl ester derivatives thereof, as defined. Exemplary acyl derivatives are the formyl, acetyl, propionyl, and succinyl derivatives, of which the formamide, acetamide and succinyl derivatives are preferred. Exemplary ester derivatives are methyl, ethyl and isopropyl esters.

The mechanism underlying the present invention is believed to be that the methionine compound acts in vivo to reduce the effect of release by polymorphonuclear leuckocytes (PMNs) of hypochlorous acid and other oxidants so that systemic oxidation, proteolysis, and tissue damage are inhibited. It is believed that the l-form of the methionine compound serves to fulfill its essential, recognized nutritional need whereas it is the d-form that has a previously unrecognized potent and different action at high dosage which is a well tolerated antiinflammatory activity.

In trials where the antioxidant activity was compared with that of ascorbic acid (a known antioxidant substance), methionine, methionine sulfoxide, S-Methyl cysteine, and vitamin U (S-Methyl methionine), were mixed with an equimolar amount of vitamin C (ascorbic acid) and then titrated with sodium hypochlorite. Methionine was three times better (equimolar basis) than vitamin C as an antioxidant for HOCl. S-Methyl cysteine had about the same level of antioxidant activity as methionine. Methionine sulfoxide and vitamin U did not affect the oxidation of vitamin C by sodium hypochlorite (as measured by the decrease in ultravio let absorption at 270 nanometers). Thus, neither S-methyl methionine nor methionine sulfoxide are suitable for reducing the effect of hypochlorous acid produced by PMNs (neutrophils).

In contrast to vitamin C which has limited oral uptake of about 100 mg per day methionine can be elevated to quite high levels (up to 25 times normal levels) in the body by administration of methionine. Spaced administration of 1.5 grams of d-methionine results in a 3 fold increase in blood levels of methionine. Because d-methionine has a much longer half-life than l-methionine and because d-methionine is transported into the brain while most otherd-amino acids to not penetrate the blood-brain barrier, it is anticipated that when dl- or d-methionine is administered with other dietary antioxidants a synergistic effect of overall antioxidant effect will be seen. Synergistic antioxidant effects can be detected in humans with arthritis by measuring the reduction of blood levels of mixed cysteine/homocysteine disulfides.

To the extent that conditions benefited by the consumption of dl-methionine are the result of a dietary deficiency of l-methionine it may be desirable to replenish methionine in food products as is currently done for a number of vitamins that are also made unavailable by food processing. The invention also employs methods for providing methionine in the final product for consumption in the amount that provides for replacement of unavailable methionine and additional methionine that would accomplish the teachings herein where it is desirable to obtain the additional antioxidant amount in a normal food item.

Damico (U.S. Pat. No. 3,952,115) teaches the addition of N-acyl l-methionine as a preferred method to reduced undesired effects of methionine supplementation. He teaches that the amount of methionine to be added to methionine-deficient protein can be determined by amino acid analysis in the case of proteins known to be low in methionine content such that methionine should be added up to the level characteristic for egg protein (an amount recognized by the U.S. Food and Drug administration as the upper limit for addition of methionine for commercial foods). In the case of proteins for which methionine is lost by food processing such as extracted protein of soy bean he teaches that the amount of methionine to be added for proper nutrition involves adding methionine derivatives as determined by rodent feeding experiments.

Because of the role that inflammatory cells play in long term tissue damage and because of the known dietary correlations of several serious inflammatory pain conditions that may be affected by reduced control of inflammatory cells, correction of a chronic marginal dietary deficiency of methionine and thus improved long term control of inflammatory cells can be expected to reduce the severity or incidence of these conditions. As an example of the possible contribution of reduced control of inflammatory cells, especially PMNs, that may be due to a marginal dietary deficiency of available methionine, it has been shown that products of stimulated PMNs can cause cellular transformation, a characteristic that has been associated with carcinogenesis (Weitzman, et. al., Science, 227: 1231-3, 1985). Smokers that have been exposed to asbestos have very much higher lung cancer rates than exposed non-smokers, and it has been shown that smoking oxidizes a methionine residue in alpha1-protease inhibitor, thus allowing increased lung proteolysis. Other examples include arthritis and migraine headaches.

It is found according to the invention that methionine, by its systemic antioxidant effect, especially d-methionine in humans and N-acetyl d-methionine in animals, systemically reduces the activity of immunocytes, especially polymorphonuclear neutrophils (PMNs).

The best method to practice the teachings of described compounds depends on the particular conditions being treated and the compositions that are required to produce optimal results. In those cases where the methionine compound is l-, dl-methionine or a derivative of l- or dl-methionine the inclusion of homocysteine affecting amino acids and homocysteine affecting vitamins assures adequate conversion of homocysteine to cysteine or the methylation of homocysteine to methionine. In addition, in those cases where other dietary antioxidants may limit the total benefit to be derived from methionine compounds they should be provided with the methionine compounds. When methionine compounds are used in the upper portion of the dosage range dissolution of the compound in the stomach should be slowed. Also, individuals that are more sensitive to gastric upset should be provided with slow dissolving compositions to get effective relief.

The method for treating ischemic or thrombotic disease response in a subject preferably comprises administering in the dosage form with the methionine compound at least one homocysteine reducing or remethylating compound sometimes referred to herein as a homocysteine affecting compound. The homocysteine affecting compound is at least one homocysteine affecting amino acid or homocysteine affecting vitamin selected from the group consisting of glycine, serine, vitamin B12, vitamin B6, and folic acid or folate, the compound being present in an amount sufficient to enable the systemic conversion of homocysteine to methionine or cysteine. The metabolic pathways for such conversion are detailed in: Biochemistry—A Case Oriented Approach, Montgomery, Dryer, Conway, Spector, eds., Mosby Co., London, IV Ed., 1983, p. 466-70; and: Fleisher and Gaull, Clinics in Endocrinology and Metabolism, 3:37-55, 1974; incorporated herewith by reference. Background for this is that methionine may have an adverse effect when given to subjects with vitamin B12 or folate deficiency. This effect is thought to be due to a buildup of systemic homocysteine; homocysteine is poorly remethylated in the absence or deficiency of vitamin B12 or folate. Also, the vitamin B6 level may be too low for the metabolism of homocysteine to cysteine by way of cystathionine. Thus, chronic comsumption of excess l-methionine, for example, may result in mild homocysteine elevation unless other co-factor substances are used or supplemented to stimulate the transformation of the excess homocysteine. The buildup is avoided, according to the invention, by including at least one homocysteine affecting compound in the dosage: vitamin B12 and folate to insure that homocysteine can be systemically remethylated to methionine; glycine or serine to insure that homocysteine can be reduced by way of cystathionine to cysteine; and vitamin B6 to insure that homocysteine can be metabolized to cysteine. The amino acids glycine and serine preferably are present in the serving or dosage in an amount from 1/5 to 3 times the amount of methionine compound. The nutrients, vitamins B12, B6 or folate preferably are present in the total daily dosage range of: B12, 0.3 to 30 micrograms; B6, 0.2 to 20 milligrams; folate, 40 to 4000 micrograms; and combinations thereof.

INFLAMMATORY ISCHEMIA AND THROMBOSIS

In one preferred method aspect, the inventive concerns a method for inhibiting an inflammatory ischemic, reperfusion ischemic, or thrombotic disease response in a subject. Ischemia occurs as well in toxic shock syndrome and hypovolemic shock. The method comprises administering to the subject a composition in dosage form suitable for oral or intravenous administration comprising an effective antiinflammatory amount of at least one methionine compound as defined above, preferably at least 0.5 grams of methionine content per unit dose, preferably in dl-form, and a coagulant inhibitor in an anticoagulant effective amount, preferably at least one such inhibitor selected from the group including aspirin (an antiinflammatory), dipryidamole (a coronary vasodilator), sulfinpyrazone (for its art-recognized uricosuric effect), and dextran (e.g. Dextran 40, a blood flow promoter or adjuvant) or other similar art-recognized substances for anticoagulation, coronary dilation, uricosuric or blood flow promoter effects, and combinations thereof (as detailed, e.g., in The Nurses Guide to Drug Therapy, op. cit., p. 510-20, and incorporated herewith by reference).

In another preferred aspect, the method employs a ischemia therapeutic antiinflammatory composition in unit dosage form suitable for oral or intravenous administration comprising an antiinflammatory effective amount of at least one methionine compound as defined above, and at least one member from the groups (a) through (e); (a) at least one homocysteine affecting amino acid, as defined above, in an amount sufficient to enable the systemic conversion, when consumed or administered of homocysteine to cysteine, (b) at least one homocysteine affecting vitamin as defined above, in an amount sufficient to enable the systemic conversion, when consumed or administered, of homocysteine to methionine or cysteine, (c) at least one coagulation inhibitor in a symptom relieving amount, as defined above, (d) at least one dietary antioxidant in a synergistically antioxidants effective amount selected from a group of dietary antioxidants including vitamins A,C,E, selenium, or zinc, where the total daily dosage range for each is: vitamin A, 500 to 50,000 IU; vitamin C, 1 to 1000 mg; vitamin E, 1 to 150 IU; selenium, 1 to 200 mcg; zinc, 1 to 150 mg; and combinations thereof; (e) an inactive excipient that provides insolubility in the stomach and solubility in the intestines or excipients that make the compounds suitable for systemic administration; and (f) combinations thereof. By using agents different in mechanism of action and agents having similar mechanisms of action, a synergistic antiinflammatory or anticoagulant effect can be expected.

LIPID NORMALIZATION

In one preferred method aspect, the invention concerns a method for inhibiting cholesterolemic disease response in a subject. The method comprises administering to the subject a composition in dosage form comprising an effective cholesterol lowering amount amount of at least one methionine compound as defined above, and the amino acids glycine or serine in a homocysteine lowering amount, as shown above.

For example, in a case of subject exhibiting an elevated serum cholesterol level, it was found that oral administration of a composition containing methionine (dl-form) according to the invention for an extended daily regimen resulted in lowering the serum cholesterol level from 232 to 196 mg/dl. In animal experiments where rats are fed large amounts of cholesterol, methionine raises blood cholesterol with 25% protein but lowers cholesterol on low protein diets. At all levels of protein the combination of glycine and methionine lowers cholesterol. However, in these animals the combination of methionine and glycine does not cause a lowering of triglycerides. (Sugiyama, Agric. Biol. Chem. 49: 3455-3461, 1985).

For normalizing cholesterol levels in a human, the methionine compound is administrated in a daily oral dose, in the range from 1.0 to 10 grams per 70 kg of body weight until the cholesterol levels are normalized. The glycine or serine compound is coadministered in the range of 1/5 to 3 times the amount of methionine compound until the homocysteine levels are normalized.

In another preferred aspect, the method employs a dietary or therapeutic lipid normalizing composition in unit dosage form or serving, comprising a cholesterol normalizing amount of at least one methionine compound as defined above and at least one member from the groups (a) through (d); (a) at least one homocysteine affecting amino acid as defined above, in an amount sufficient to enable the systemic conversion of homocysteine to cysteine, (b) at least one homocysteine affecting vitamin as above, in an amount sufficient to enable the systemic conversion, when consumed or administered, of homocysteine to methionine or cysteine, (c) at least one anticholesterolemic such as cholestyramine, clofibrate, gemfibrozil, and nicotinic acid, preferably in a per se art-recognized unit dose amount, as defined above, (d) an inactive excipient that provides insolubility in the stomach and solubility in the intestines; and (e) combinations thereof. Because the mechanism of effect of methionine on lipid metabolism is different from other agents that lower blood cholesterol a synergistic lipid normalizing effect can be expected.

To the extent that elevated blood cholesterol is the result of a dietary deficiency of methionine it may be desirable to replenish methionine in food products. The invention also concerns a method for providing methionine in the final product for consumption, in the amount of from more that 3 grams total methionine but less than about 15 grams methionine per 100 grams total protein. The invention also concerns a method of combining glycine or serine with methionine compound (n=2, dl- or l-) to be added to food products so as to avoid elevated homocysteine.

PREPARATION OF PHARMACEUTICAL COMPOSITIONS

When being utilized as pharmacological agents, the compounds of the invention can be prepared and administered in a wide variety of oral and parenteral dosage forms. It will be clear to those skilled in the art that the following dosage forms may comprise as the active component, one or more compounds of formula I, corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredients. Suitable solid carriers are magnesium carbonate, magnesium steareate, talc, sugar, lactose, pectin, dextrin, starch, gelatin, tragacanth, methyl cellulose, sodium carboxymethyl cellulose, a low melting point wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include dusting powders, creams, lotions, gels, and sprays. These various topical preparations may be formulated by well-known procedures. See for example Remington's Pharmaceutical Sciences, p. 773-85, and 1585-602, 17th Ed., 1985, Mack Publishing Co., Easton, Pa.

Preferably, the pharmaceutical preparation is in unit dosage form. In such form, the preparation is subdivided into unit doses containing appropriate quantities of the active component. The unit dosage form can be a packaged preparation, the package containing descrete quantities of preparation, for example, packeted tablets, capsules, and powders in vials or ampoules. The unit dosage form can also be a capsule, cachet, or tablet itself or it can be the appropriate number of any of these package forms.

The quantity of active compound in a unit dose of preparation may be varied or adjusted from 100 to 1000 mg. according to the particular application and the potency of the active ingredient.

In therapeutic use as pharmacological agents the compounds utilized in the pharmaceutical method of this invention are administered at the initial dosage of about 10 to about 50 mg per kilogram. A dose range of about 15 mg to about 30 mg per kilogram is preferred. The dosages, however, may be varied depending upon the severity of the condition being treated, and compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired. The dosage preferably is in a sustained or controlled release form (e.g. an enteric coated or slow release dosage form) to insure that the dosage is released in the intestine and a uniformly elevated blood level of the methionine compound is achieved, as described above.

The active compounds may also be administered parenterally or intraperitoneally. Solutions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain preservatives to prevent the growth of microorganisms.

The pharmaceutical forms suitable for injectable use include sterile aqueous solutions or dispersions and sterile powders for the extemporaneous preparation of sterile injectable solutions or dispersions. These various injectables may be formulated by well-known procedures. See for example Remington's Pharmaceutical Sciences, Chapter 86, 17th Ed., 1985, Mack Publishing Co., Easton, Pa. In all cases the form must be sterile and must be fluid to the extent that easy syringability exists. It must be stable under the conditions of manufacture and storage and must be preserved against the contaminating action of microorganisms such as bacteria and fungi. The carrier can be solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredients into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterilefiltered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage forms used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compounding such an active material for the treatment of disease in living subjects having a disease condition in which bodily health is impaired as herein disclosed in detail.

The principal active ingredient is compounded for convenient and effective administration in effective amounts with a suitable pharmaceutically-acceptable carrier in unit dosage form as hereinbefore disclosed. A unit dosage form can, for example, contain the principal active compound in amounts ranging from about 500 to about 10,000 mg, with from about 1,000 to about 2,000 mg being preferred. Expressed in proportions, the active compound is generally present in from about 50 to about 500 mg/ml of carrier. In the case of compositions containing supplementary active ingredients, the dosages are determined by reference to the usual dose and the manner of administration of the said ingredients. The daily parenteral doses for lower mammalian subjects to be treated ranges from about 1 to 100 mg/kg. The preferred daily dosage range is about 2 to 20 mg/kg.

The invention and the best mode of practicing the same are illustrated by the following examples of preferred embodiments of selected compounds and their preparation.

EXAMPLE 1

CAPSULES
Example 1a
d-Methionine
100 mg, 250 mg or 500 mg

| | |
|---|---|
| d-Methionine | 500 g |
| Lactose USP, Anhydrous q.s. or | 200 g |
| Sterotex Powder HM | 5 g |

Combine the methionine and the Lactose in a twinshell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg., 352.5 mg., or 705 mg. of the blend, respectively, for the 100 mg., 250 mg., and 500 mg. containing capsules.

| Example 1b dl-Methionine 100 mg, 250 mg or 500 mg | |
|---|---|
| dl-Methionine | 500 g |
| Lactose USP, Anhydrous q.s. or | 200 g |
| Sterotex Powder HM | 5 g |

Mix and fill as per Example 1a.

EXAMPLE 2

| TABLETS | |
|---|---|
| The Methionine Compound | 250 g |
| Corn Starch NF | 200 g |
| Cellulose, Microcrystalline | 46 g |
| Sterotex Powder HM | 4 g |
| Purified Water q.s. | 300 ml |

Combine the corn starch, the cellulose and the methionine compound together in a planetary mixer and mix for two minutes. Add the water to this combination and mix for one minute. The resulting mix is spread on trays and dried in a hot air oven at 50 degrees C. until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of 100 mg., 500 mg., and 1000 mg. respectively, of the total mix are formed with appropriate sized punches for the 50 mg., 250 mg., or 500 mg. containing tablets.

EXAMPLE 3

| SUPPOSITORIES Example 3a d-Methionine 125 mg, 250 mg, or 500 mg per 3 G | | | |
|---|---|---|---|
| dl-Methionine | 125 mg | 250 mg | 500 mg |
| Polyethylene Glycol 1540 | 1925 mg | 1750 mg | 1400 mg |
| Polyethylene Glycol 8000 | 825 mg | 750 mg | 600 mg |

Melt the Polyethylene Glycol 1540 and the Polyethylene Glycol 8000 together at 60 degrees C. and dissolve dl-Methionine into the melt. Mold this total at 25 degrees C. into appropriate suppositories.

| Example 3b dl-Methionine 125 mg, 250 mg, or 500 mg per 3 G | | | |
|---|---|---|---|
| dl-Methionine | 125 mg | 200 mg | 500 mg |
| Polyethylene Glycol 1540 | 1925 mg | 1750 mg | 1400 mg |
| Polyethylene Glycol 8000 | 825 mg | 750 mg | 600 mg |

Prepare as per Example 3a above.

EXAMPLE 4

Preparation of Intravenous Formulations

A solution of from 25 to 50 grams of dl-Methionine is prepared in 1 liter of water for injection at room temperature with stirring. The solution is sterile filtered into 500 5-ml vials, each of which contains 2 ml of solution containing 50 to 100 mg of compound, and sealed under nitrogen.

In addition, other desired active ingredients, such as those listed above for preferred tablet formulations, may be added in appropriate unit dosage amounts before the solution is sterile filtered.

Alternatively, after sterile filtration into vials, the water may be removed by lyophilization, and the vials then sealed aseptically, to provide a powder which is redissolved in the desired unit dosage concentration prior to injection.

In another preferred aspect, the method employs a ischemia therapeutic antiinflammatory composition in unit dosage form suitable for oral or intravenous administration comprising an antiinflammatory effective amount of at least one methionine compound as defined above, and at least one member from the groups (a) through (e); (a) at least one homocysteine affecting amino acid from the group of glycine and serine, in an amount sufficient to enable the systematic conversion, when consumed or administered, of homocysteine to cysteine, (b) at least one homocysteine affecting vitamin in an amount sufficient to enable the systemic conversion, when consumed or administered, of homocysteine to methionine or cysteine, selected from the group consisting of vitamins B12, B6, and folic acid where the total daily dosage range for each is: vitamin B12, 0.3 to 30 mcg; vitamin B6, 0.2 to 20 mg; folic acid, 40 to 4000 mcg, and combinations thereof; (c) at least one coagulation inhibitor in an anticoagulant effective amount, preferably selected from the group including aspirin (an antiinflammatory), dipryidamole (a coronary vasodilator), sulfinpyrazone (for its art-recognized uricosuric effect), and dextran (e.g. Dextran 40, a blood flow promoter or adjuvant) or other similar art-recognized substances for anticoagulation, coronary dilation, uricosuric or blood flow promoter effects, and combinations thereof; (d) at least one dietary antioxidant in a synergistically antioxidant effective amount selected from a group of dietary antioxidants including vitamins A,C,E, selenium, or zinc, where the total daily dosage range for each is: vitamin A, 500 to 50,000 IU; vitamin C, 1 to 1000 mg; vitamin E, 1 to 150 IU; selenium, 1 to 200 mcg; zinc, 1 to 150 mg; and combinations thereof; (e) an inactive excipient that provides insolubility in the stomach and solubility in the intestines or excipients that make the compounds suitable for systemic administration; and (f) combinations thereof. By using agents different in mechanism of action and agents having similar mechanisms of action, a synergistic antiinflammatory or anticoagulant effect can be expected.

Having thus described our invention, what we claim and desire by Letters Patent to secure are the following:

1. A method for inhibiting inflammatory ischemic, thrombotic and cholesterolemic disease response in a subject in need of such treatment, comprising administration to the subject in oral dosage form an antiinflammatory effective amount of at least one methionine compound selected from the group consisting of the methionine hydroxy analogs, and methionine compounds having the structural formula I

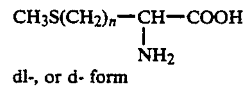

and pharmaceutically acceptable N- (mono- and di-carboxylic acid) acyl derivatives of methionine and alkyl esters of methionine compounds and analogs, where n is an integer from 1 to 3.

2. A method according to claim 1 where the methionine compound is in the dl-form.

3. A method according to claim 1 where the methionine compound is in the d-form.

4. A method according to claim 1 where the methionine compound is administered in a daily dosage in the range from 1.0 to 10 grams per 70 kg. of body weight until the inflammation is relieved.

5. A method according to claim 1 where the dosage form contains in addition at least one homocysteine affecting vitamin selected from the group consisting of vitamin B12, B6, or folic acid, in an amount sufficient to enable the systemic conversion of excess homocysteine present in the system to methionine and cysteine, where the total daily dosage range of vitamin B12, B6 or folic acid corresponds to: vitamin B12, 0.3 to 30 micrograms; vitamin B6, 0.2 to 20 milligrams; folic acid, 40 to 4000 micrograms; and combinations thereof.

6. A method according to claim 1 where the dosage form contains in addition one homocysteine affecting amino acid selected from the group consisting of serine and glycine, in an amount sufficient to enable the systemic conversion of excess homocysteine present in the system to cysteine, said amount ranging from 1/5 to 3 times the methionine compound.

7. A method according to claim 1 where the dosage form contains in addition at least one dietary antioxidant in an effective amount selected from a group of dietary antioxidants including vitamins A, C, E, selenium and zinc, where the total daily dosage range for each is: vitamin A, 500 to 50,000 IU; vitamin C, 1 to 1000 mg; vitamin E, 1 to 150 IU; selenium, 1 to 200 mcg; zinc, 1 to 150 mg; and combinations thereof.

8. A method according to claim 1 where the dosage form contains in addition a coagulation inhibitor in an anticoagulant effective amount, such inhibitor selected from the group including aspirin, dipryidamole, lovastatin, clofibrate, and Dextran 40.

9. A method according to claim 1 for inhibiting inflammatory response in dogs, cows, pigs or cats where the methionine compound is administered as an N-acyl compound in a daily dosage in the range of 5 to 100 milligrams per kg. of body weight until the inflammation is relieved.

10. A method for inhibiting cholesterolemic disease response in a subject in need of such treatment, comprising provision to the subject a foodstuff comprising essentially the food ingredient and a nutritionally adequate amount of a methionine compound as determined by human nitrogent balance studies or other methods validated thereby, selected from the group consisting of the methionine hydroxy analogs, and l- and dl-methionine compounds; and pharmaceutically acceptable N-(mono- and di-carboxylic acid) acyl derivatives of methionine and alkyl esters of methionine compounds and analogs.

11. A method according to claim 10, suitable for administration to persons in an institutional setting where the methionine compound is sufficient to provide total l-methionine content in the final food product of more than 3 grams l-methionine per 100 grams protein but less 15 grams of l-methionine compound per 100 grams protein.

12. A method according to claim 10 where the methionine compound is in the dl-form.

13. A method according to claim 10 where the methionine compound is in the l-form.

14. A method according to claim 10 where the dosage form contains in addition at least one homocysteine affecting vitamin selected from the group consisting of vitamin B12, B6, or folic acid, in an amount sufficient to enable the systemic conversion of excess homocysteine present in the system to methionine and cysteine, where the total daily dosage range of vitamin B12, B6 or folic acid corresponds to: vitamin B12, 0.3 to 30 micrograms; vitamin B6, 0.2 to 20 milligrams; folic acid, 40to 4000 micrograms; and combinations thereof.

15. A method according to claim 10 where the dosage form contains in addition one homocysteine affecting amino acid selected from the group consisting of serine and glycine, in an amount sufficient to enable the systemic conversion of excess homocysteine present in the system to cysteine, said amount ranging from 1/5 to 3 times the methionine compound.

16. A method according to claim 10 where the dosage form contains in addition at least one dietary antioxidant in a synergistically antioxidant effective amount selected from a group of dietary antioxidants including vitamins A,C,E, selenium, and zinc, where the total daily dosage range for each is: vitamin A, 500 to 50,000 IU; vitamin C, 1 to 1000 mg; vitamin E, 1 to 150 IU; selenium, 1 to 200 mcg; zinc, 1 to 150 mg; and combinations thereof.

* * * * *